(12) United States Patent
Liu et al.

(10) Patent No.: US 11,988,640 B2
(45) Date of Patent: May 21, 2024

(54) BOTTOM ELECTRODE MATERIAL STACK FOR MICROMACHINED ULTRASONIC TRANSDUCER DEVICES (71) Applicant: BFLY OPERATIONS, INC., Burlington, MA (US)

(72) Inventors: Jianwei Liu, Fremont, CA (US); Lingyun Miao, Fremont, CA (US); Victor L. Pushparaj, Milpitas, CA (US)

(73) Assignee: BFLY OPERATIONS, INC., Burlington, MA (US)

( * ) Notice: Subject to any disclaimer, the term of this patent is extended or adjusted under 35 U.S.C. 154(b) by 509 days.

(21) Appl. No.: 17/198,174

(22) Filed: Mar. 10, 2021

(65) Prior Publication Data

US 2021/0285917 A1 Sep. 16, 2021

Related U.S. Application Data (60) Provisional application No. 62/988,290, filed on Mar. 11, 2020.

(51) Int. Cl.
*G01N 29/24* (2006.01)
*A61B 8/00* (2006.01)
*B06B 1/02* (2006.01)
*B81B 7/00* (2006.01)
*B81C 1/00* (2006.01)

(52) U.S. Cl.
CPC ....... *G01N 29/2406* (2013.01); *A61B 8/4483* (2013.01); *B06B 1/0292* (2013.01); *B81B 7/007* (2013.01); *B81C 1/00166* (2013.01)

(58) Field of Classification Search
CPC .......... G01N 29/2406; A61B 8/4483; B06B 1/0292; B81B 7/007; B81C 1/00166
See application file for complete search history.

(56) References Cited

U.S. PATENT DOCUMENTS

| | | | |
|---|---|---|---|
| 9,067,779 B1 | 6/2015 | Rothberg et al. | |
| 9,242,275 B2 | 1/2016 | Rothberg et al. | |
| 9,499,392 B2 | 11/2016 | Rothberg et al. | |
| 9,505,030 B2 | 11/2016 | Rothberg et al. | |
| 10,672,974 B2 | 6/2020 | Rothberg et al. | |
| 10,856,844 B2 | 12/2020 | Fife et al. | |
| 2011/0055447 A1 | 3/2011 | Costa | |
| 2012/0119621 A1* | 5/2012 | Frey | H02N 2/18 310/330 |
| 2014/0375168 A1* | 12/2014 | Dirksen | B81C 1/00373 427/79 |
| 2015/0368162 A1* | 12/2015 | Hayashi | B41J 2/14201 347/68 |
| 2019/0001159 A1 | 1/2019 | Chen et al. | |
| 2019/0231312 A1 | 8/2019 | Fife et al. | |

(Continued)

*Primary Examiner* — Thomas Truong
(74) *Attorney, Agent, or Firm* — Carter, DeLuca & Farrell LLP (57) ABSTRACT An ultrasonic transducer device includes a bottom electrode layer of a transducer cavity disposed over a substrate. The bottom electrode layer includes a bottom layer of a first type metal; a top layer of the first type metal; a second type metal disposed between the bottom layer and the top layer; and at least one intermediate layer of the first type metal disposed between the bottom layer and the top layer, the at least one intermediate layer configured so as to define at least two discrete layers of the second type metal.

14 Claims, 6 Drawing Sheets

(56) References Cited

U.S. PATENT DOCUMENTS

| | | |
|---|---|---|
| 2019/0275561 A1 | 9/2019 | Fife et al. |
| 2019/0336099 A1 | 11/2019 | Fife et al. |
| 2019/0336104 A1 | 11/2019 | Fife et al. |
| 2020/0013691 A1 | 1/2020 | Liu et al. |
| 2020/0102214 A1 | 4/2020 | Liu et al. |
| 2020/0147641 A1 | 5/2020 | Fife et al. |
| 2020/0156110 A1 | 5/2020 | Miao et al. |
| 2020/0184176 A1 | 6/2020 | Liu et al. |
| 2020/0184177 A1 | 6/2020 | Liu et al. |
| 2020/0239299 A1 | 7/2020 | Liu et al. |
| 2020/0254487 A1 | 8/2020 | Miao et al. |
| 2020/0269279 A1 | 8/2020 | Miao et al. |
| 2020/0324318 A1 | 10/2020 | Liu et al. |
| 2020/0324319 A1 | 10/2020 | Miao et al. |
| 2020/0348794 A1 | 11/2020 | Ralston et al. |
| 2020/0349342 A1 | 11/2020 | Ralston et al. |
| 2021/0038193 A1 | 2/2021 | Liu et al. |

\* cited by examiner

BOTTOM ELECTRODE MATERIAL STACK FOR MICROMACHINED ULTRASONIC TRANSDUCER DEVICES

CROSS-REFERENCE TO RELATED APPLICATIONS

The present application claims the benefit under 35 U.S.C. § 119(e) of U.S. Patent Application Ser. No. 62/988,290, filed Mar. 11, 2020, and entitled "BOTTOM ELECTRODE MATERIAL STACK FOR MICROMACHINED ULTRASONIC TRANSDUCER DEVICES," which is hereby incorporated by reference herein in its entirety.

FIELD

The present disclosure relates generally to micromachined ultrasonic transducers and, more specifically, to a bottom electrode material stack for micromachined ultrasonic transducer cavities.

BACKGROUND

Ultrasound devices may be used to perform diagnostic imaging and/or treatment, using sound waves with frequencies that are higher than those audible to humans. When pulses of ultrasound are transmitted into tissue, sound waves are reflected off the tissue with different tissues reflecting varying degrees of sound. These reflected sound waves may then be recorded and displayed as an ultrasound image to the operator. The strength (amplitude) of the sound signal and the time it takes for the wave to travel through the body provide information used to produce the ultrasound images.

Some ultrasound imaging devices may be fabricated using micromachined ultrasonic transducers, including a flexible membrane suspended above a substrate. A cavity is located between part of the substrate and the membrane, such that the combination of the substrate, cavity and membrane form a variable capacitor. When actuated by an appropriate electrical signal, the membrane generates an ultrasound signal by vibration. In response to receiving an ultrasound signal, the membrane is caused to vibrate and, as a result, generates an output electrical signal.

SUMMARY

In one aspect, an ultrasonic transducer device includes a bottom electrode layer of a transducer cavity disposed over a substrate. The bottom electrode layer includes a bottom layer of a first type metal; a top layer of the first type metal; a second type metal disposed between the bottom layer and the top layer; and at least one intermediate layer of the first type metal disposed between the bottom layer and the top layer, the at least one intermediate layer configured so as to define at least two discrete layers of the second type metal.

In another aspect, a method of forming an ultrasonic transducer device includes forming a bottom layer of a first type metal over a substrate; forming a second type metal over the bottom layer; forming a top layer of the first type metal over the second type metal; and forming at least one intermediate layer of the first type metal between the bottom layer and the top layer, the at least one intermediate layer configured so as to define at least two discrete layers of the second type metal, wherein the bottom layer, the at least one intermediate layer, the at least two discrete layers and the top layer define a bottom electrode layer of a transducer cavity.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIGS. 2-1 through 2-3 are a series of cross-sectional views illustrating some processing operations that may be performed in fabricating a micromachined ultrasonic transducer device.

FIG. 2-3A is an enlarged view of the dashed portion of FIG. 2-3.

FIGS. 4-1 through 4-3 are a series of cross-sectional views illustrating some processing operations that may be performed in fabricating a micromachined ultrasonic transducer device, according to one embodiment.

DETAILED DESCRIPTION

The techniques and structures described herein relate to micromachined ultrasonic transducer (MUT) devices having enhanced reliability. In one aspect, a bottom transducer electrode stack has a double or multiple sandwiched structure of first and second type metals that results in reduced grain size formation in the stack layers. This in turn may provide improved smoothness of the transducer cavity bottom layer, and in turn improved device performance and reliability.

One type of transducer suitable for use in ultrasound imaging devices is a MUT, which can be fabricated from, for example, silicon and configured to transmit and receive ultrasound energy. MUTs may include capacitive micromachined ultrasonic transducers (CMUTs) and piezoelectric micromachined ultrasonic transducers (PMUTs), both of which can offer several advantages over more conventional transducer designs such as, for example, lower manufacturing costs and fabrication times and/or increased frequency bandwidth. With respect to the CMUT device, the basic structure is a parallel plate capacitor with a rigid bottom electrode and a top electrode residing on or within a flexible membrane. Thus, a cavity is defined between the bottom and top electrodes. In some designs (such as those produced by the assignee of the present application for example), a CMUT may be directly integrated on an integrated circuit that controls the operation of the transducer. One way of manufacturing a CMUT is to bond a membrane substrate to an integrated circuit substrate, such as a complementary metal oxide semiconductor (CMOS) substrate. This may be performed at temperatures sufficiently low to prevent damage to the devices of the integrated circuit.

Figure 1:
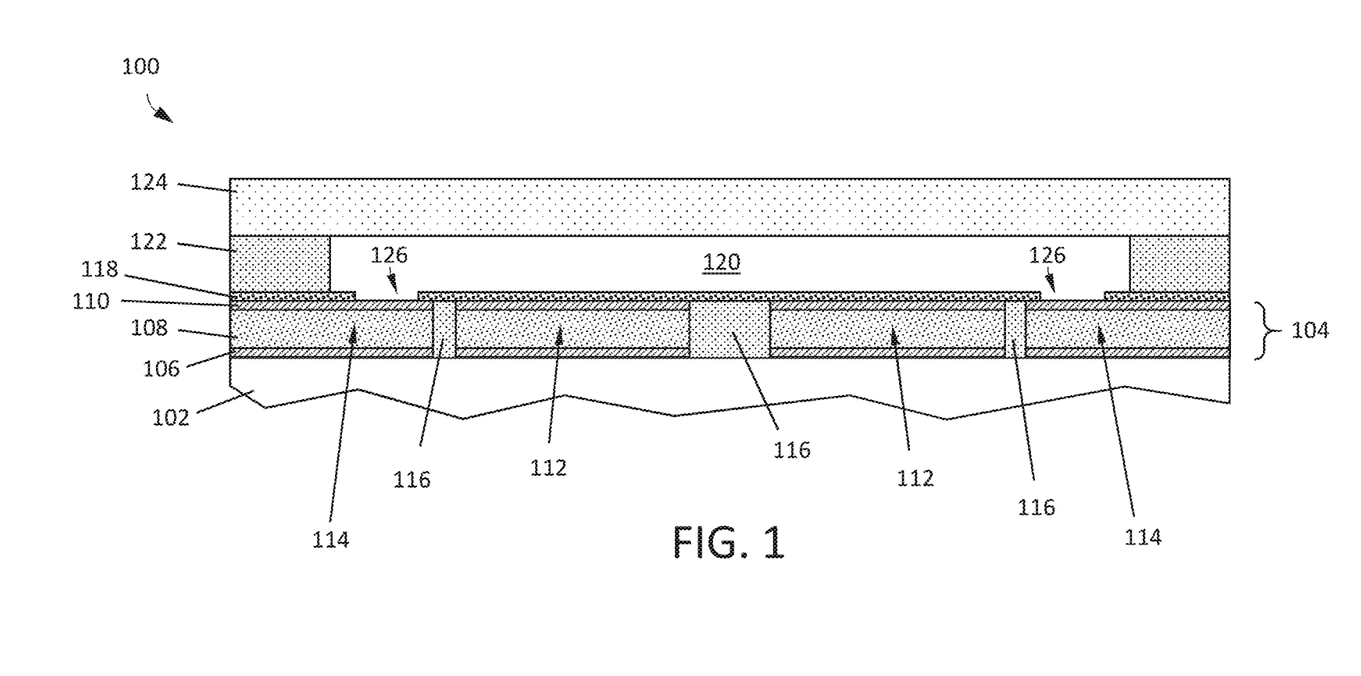
FIG. 1 is a cross-sectional view of an exemplary micromachined ultrasonic transducer device.

Referring initially to FIG. 1, there is shown a cross-sectional view of an exemplary micromachined ultrasonic transducer device 100, such as a CMUT. The transducer device 100 includes a substrate, generally designated by 102, (e.g., a CMOS substrate, such as silicon) having one or more layers, such as for example: CMOS integrated circuits and wiring layers, one more insulation/passivation layers, and one or more wiring redistribution layers. A transducer bottom electrode layer, designated generally at 104, is disposed over the substrate 102 and includes patterned regions of a metal layer stack. In the example depicted, the metal layer stack may include a first layer 106 of titanium nitride (TiN), a layer 108 of titanium (Ti) and a second layer 110 of TiN. The transducer bottom electrode layer 104 is patterned in a manner so as to define structures such as, for example, a transducer bottom electrode 112 (e.g., in a "donut" or ring configuration) and bypass metal structures 114, between which are located regions of an insulation layer 116 (e.g., silicon oxide ($SiO_2$)). It should be appreciated, however, that since specific substrate and transducer bottom electrode patterns are not the focus of the present disclosure, other such patterns are also contemplated. It should further be understood that electrical connections (e.g., such as vias) to the bottom electrode layer structures are not the focus of the present disclosure and, as such, are included within the general substrate region 102 of FIG. 1.

Still referring to FIG. 1, a bottom cavity layer 118 is disposed over the transducer bottom electrode layer 104. The bottom cavity layer 118 may include, for example, an electrically insulating, thin film layer stack including an $SiO_2$ layer deposited by chemical vapor deposition (CVD) and an aluminum oxide ($Al_2O_3$) layer deposited by atomic layer deposition (ALD). A transducer cavity 120 is defined by lithographic patterning and etching of a membrane support layer 122 that is formed on the bottom cavity layer 118. The membrane support layer 122 may be an insulating layer, such as $SiO_2$ for example, the remaining portions of which provide a support surface to which a flexible transducer membrane 124 (e.g., highly doped silicon at a concentration of about $1\times10^{18}$ atoms/cm$^3$ to about $1\times10^{19}$ atoms/cm$^3$) is bonded. In order to preserve the integrity and functionality of the various CMOS devices residing within the substrate 102 (such as CMOS circuits and wiring layers at or below bottom electrode layer 104), a relatively low temperature bonding process (e.g., less than about 450° C.) is employed for bonding the flexible transducer membrane 124 to the membrane support layer 122.

During bonding of the membrane substrate to the CMOS substrate, there may be a difference in cavity pressures across the die and wafer due to the water vapor and other gaseous byproducts and the propagation of the bond. This in turn may result in undesired variability of certain CMUT-based operating parameters such as for example, collapse voltage, as well as transmit/receive pressure sensitivity. Accordingly, it is desirable to be able to control cavity pressure within such a transducer device during the manufacturing process, as well as over the lifetime of the device. Thus, as additionally illustrated in FIG. 1, a getter opening pattern 126 may be defined (e.g., by etching) in the bottom cavity layer 118 prior to membrane bonding so as to expose a portion of the bypass metal structure 114 proximate the outer perimeter of the transducer cavity 120. For example, one possible getter opening pattern 126 may be an annular or ring-shaped pattern etched into the bottom cavity layer 118 prior to bonding of the flexible transducer membrane 124. By exposing the metal material of the bypass metal structure 114, gaseous material present in the cavity region (e.g., oxygen, nitrogen, argon, water vapor, etc.) may be consumed by the metal, resulting in a more uniform pressure across the various cavities 120 of the ultrasound device. Additional information regarding cavity gettering may be found in U.S. Patent Application Ser. No. 62/738,502, filed Sep. 28, 2018, U.S. patent application Ser. No. 16/585,283, filed Sep. 27, 2019 and Published as U.S. Pat. Pub. No. 2020/0102214 A1, U.S. patent application Ser. No. 16/680, 956, filed Nov. 12, 2019 and published as U.S. Pat. Pub. No. 2020/0147641 A1, and U.S. patent application Ser. No. 16/844,837, filed Apr. 9, 2020 and published as U.S. Pat. Pub. No. 2020/0324318 A1, all of which are assigned to the assignee of the present application, and the contents of all of which are incorporated by reference herein in their entireties.

An exemplary operating condition of the CMUT device 100 of FIG. 1 may involve the so-called "collapse mode" in which the flexible transducer membrane 124 comes into physical contact with a least a portion of the bottom cavity layer 118 due to an applied voltage across the transducer cavity 120 (e.g., applied between the doped flexible transducer membrane 124 and the transducer bottom electrode 112). Over the lifetime of such a device, certain challenges may exist with respect to maintaining device reliability (e.g., membrane stiction and/or electrical charging). Such conditions might in turn eventually degrade CMUT device performance and/or lead to reliability failures.

Consequently, certain fabrication parameters of both the flexible transducer membrane 124 and the bottom cavity layer 118 may play a significant role in device performance (e.g., surface smoothness, surface energy conditions, and other film properties such as hardness and Young's Modulus that determine the interface interactions during CMUT collapse). Generally speaking, a mechanically strong and dense film with a smooth surface is preferable in order to prevent mechanical damage such as wearing out and/or electrical charging arising from membrane collapse. Typically, the flexible transducer membrane 124 has relatively good surface conditions as a result of how the transducer cavity 120 is defined during a fabrication process. For example, the CMUT device 100 may be formed using low temperature oxide-to-oxide bonding technique in which the flexible transducer membrane 124 is covered by a layer of thermally grown $SiO_2$ having a high quality and smoothness.

Figure 21:
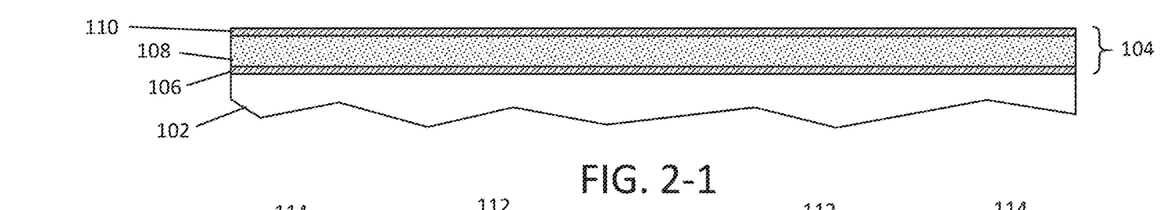
Figure 22:
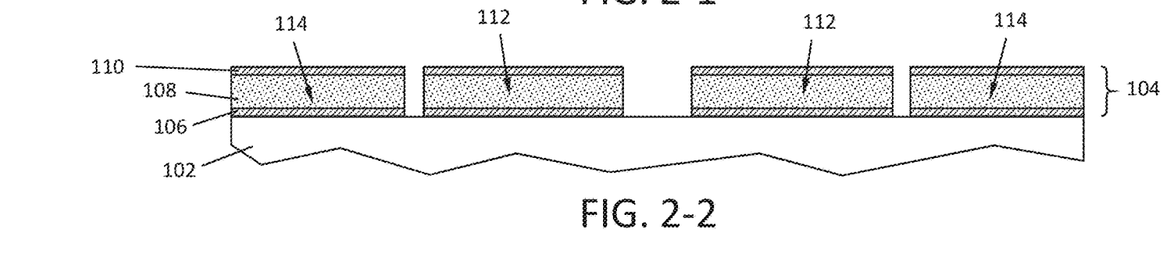
Figure 23:
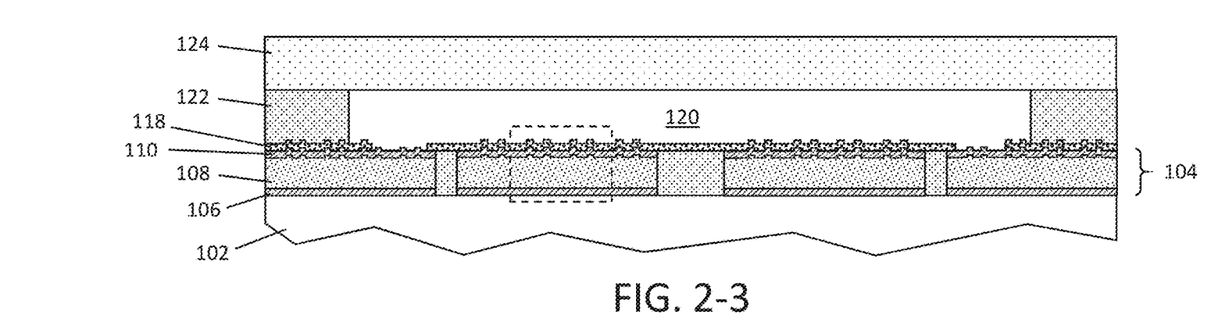
Figure 41:
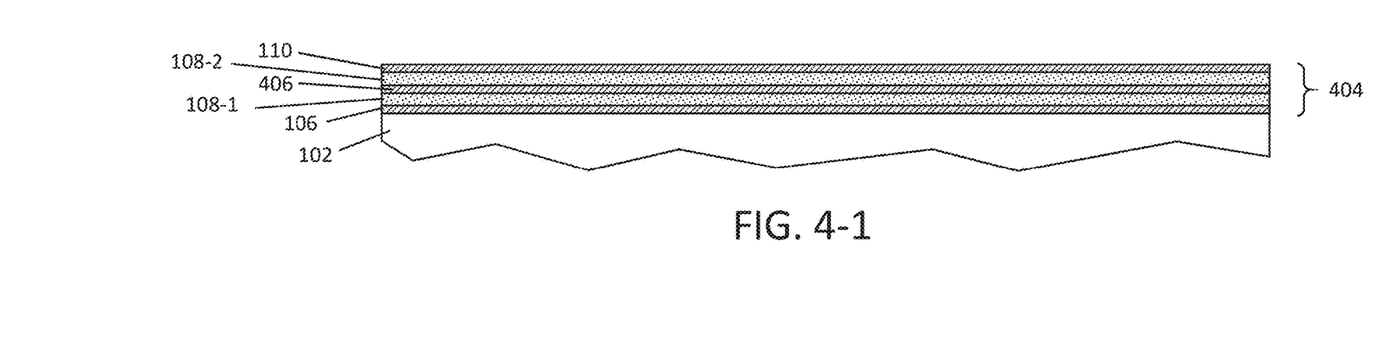
Figure 42:
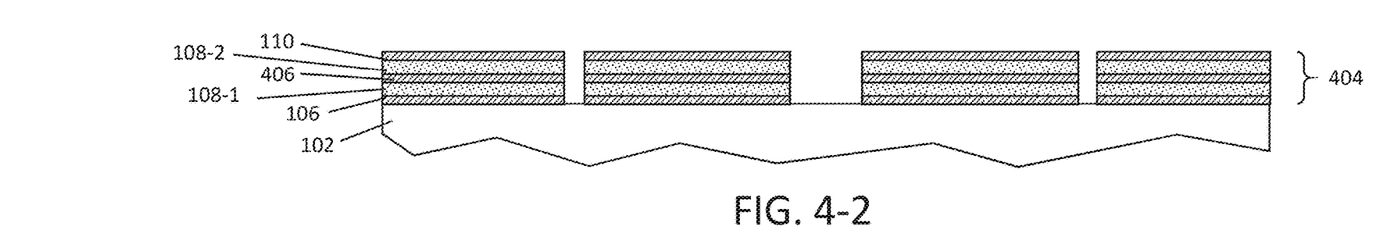
Figure 43:
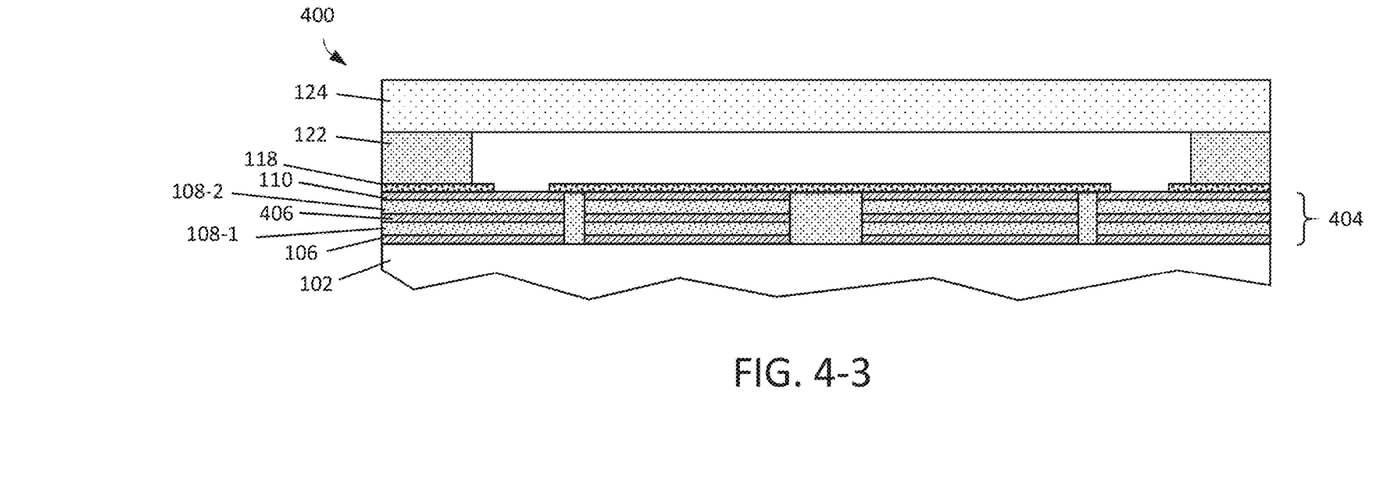

In contrast, however, the layers beneath the flexible transducer membrane 124 (e.g., the metal layer stack 106/108/110, the insulation layer 116, and the bottom cavity layer 118) undergo a series of process steps including for example: film deposition, etching, polishing, and thermal processing. As a result, these layers beneath the flexible transducer membrane 124 may be more vulnerable to surface quality degradation. By way of further illustration in this regard, reference may be made to FIGS. 2-1 through 2-3, which are a series of cross-sectional views illustrating some processing operations that may be performed in fabricating a micromachined ultrasonic transducer device. FIG. 2-1 illustrates a point in processing following deposition of the transducer bottom electrode layer 104 (metal layer stack 106/108/110) over the substrate 102, and FIG. 2-2 illustrates patterning and etching of the bottom electrode layer 104 to define the aforementioned transducer bottom electrode 112 and bypass metal structure 114. As indicated above, the transducer bottom electrode layer may be a "sandwiched" metallic structure that includes a first TiN layer 106 deposited at a thickness on the order of several hundred angstroms (e.g., about 10 nanometers (nm) to about 30 nm) and serving as a bottom seed layer, followed by a thicker Ti layer 108 deposited at a thickness on the order of several hundred to thousands of angstroms (e.g., about 10 nm to about 300 nm) and comprising a majority of the bottom electrode layer 104, and followed by a second layer 110 of TiN deposited at a thickness on the order of several hundred angstroms (e.g., about 10 nm to about 30 nm) and serving as a capping layer.

At the stage of manufacture illustrated in FIGS. 2-1 and 2-2, the bottom electrode layer 104 may still be relatively smooth and high quality as a whole. However, during subsequent downstream processes involving film stresses and elevated temperatures, one or more of the individual metal films in the stack of bottom electrode layer 104 may undergo a phenomenon known as grain formation during deposition, as well as a continuous growth of such grains in downstream process steps. Such mechanisms can in turn adversely impact the bottom cavity layer surface conditions of a completed transducer device, as shown more particularly in FIGS. 2-3 and 2-3A.

For example, in downstream processing, either higher temperature and/or stress may trigger continuous growth of Ti grains. One type of such a growth mechanism is known as "hillock growth," which describes a vertically oriented grain growth. As shown in a close-up view in FIG. 2-3A (which illustrates the dashed region of FIG. 2-3), continuously grown grains 202 of Ti from layer 108 can result in corresponding grains 204 formed in the second layer 110 of TiN (which may serve as a capping layer), as well as corresponding grains 206 formed in the dielectric layer stack of the bottom cavity layer 118. It will be noted that any such grain growth in the bottom electrode layer 104 does not necessarily affect the planarity of the membrane support layer 122, since chemical mechanical polishing (CMP) is used to planarize its topography prior to the transducer cavity etch that defines the transducer cavity 120 and exposes the bottom cavity layer 118. However, once the transducer cavity etch is performed, the bottom cavity layer 118 (and optionally a portion of the second layer 110 of TiN for gettering purposes) is again exposed before bonding of the flexible transducer membrane 124.

Though not specifically schematically depicted as such, the dimensions of the protrusions (grains 202, 204, 206) shown in FIG. 2-3A may actually vary quite a bit (e.g., with individual grain heights on the order of nanometers, and sizes ranging from tens of nanometers to hundreds of nanometers or perhaps even on a micron scale). Such variations in individual grain heights and sizes may depend, for example, on the different metal stack layers used to form the bottom electrode layer 104, as well as the thicknesses of the individual layers in the metal stack. Consequently, since some of these metal protrusions may have a concentrated high film stress, they can be easily subject to cracking when contacted by the flexible transducer membrane 124 during certain transducer operations, such as the above-mentioned collapse mode for example.

Figures 2, 3A:
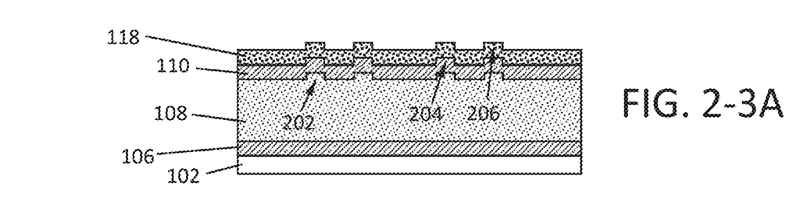
FIGS. 3A and 3B are further enlarged cross-sectional views of a micromachined ultrasonic transducer device as shown in FIG. 2-3.
Figure 3A:
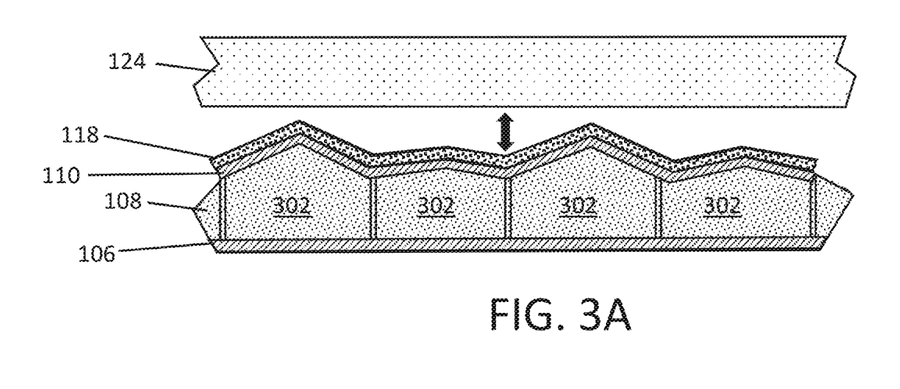
Figure 3B:
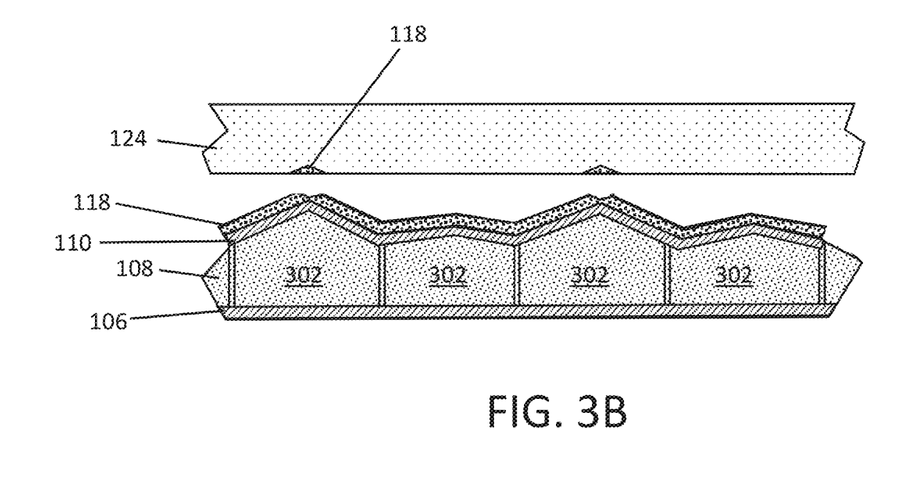

By way of further illustration, reference may be made to FIG. 3A and FIG. 3B, which depict a close-up view of the interaction between the bottom electrode layer stack and the flexible transducer membrane 124. As more specifically shown, individual metal grains 302 of varying heights and sizes define protrusions inside the transducer cavity as discussed above. The flexible transducer membrane 124 is capable of moving vertically with respect to the bottom electrode layer stack due to varying applied voltage therebetween, as shown in FIG. 3A. However, during conditions such as a collapse mode of operation, the physical impact from flexible transducer membrane 124 continuously hitting the protruded regions of the grains 302 (also having high local film stress) can result in cracking of the protrusions and, in some situations, transfer of the dielectric materials of the bottom cavity layer 118 onto the flexible transducer membrane 124 as illustrated in FIG. 3B. Consequently, the overall transducer device reliability may be compromised, possibly resulting in device failure mechanism such as, for example, breakdown and stiction.

Ultimately, the final grain size of a TiN/Ti/TiN layer structure, such as the stack 106/108/110, is proportional to the thickness of the Ti layer 108, since this layer represents a majority of the thickness of the entire layer stack used to form the bottom electrode layer 104. Moreover, once a grain begins to grow vertically (i.e., the above mentioned "hillock growth"), the grain continues to grow throughout remaining processing operations.

Accordingly, the inventors herein have recognized that by introducing one or more intermediate layers of TiN within the overall thickness of the Ti layer, a relatively thick Ti layer can instead be substituted with multiple thinner Ti layers separated by TiN layers, which in turn reduces the overall size of any hillocks or grains that may form in the Ti. In one embodiment, this may be implemented by forming a "double sandwiched" structure including a metal stack of TiN/Ti/TiN/Ti/TiN to serve as a bottom electrode layer. Such a double sandwiched structure (e.g., by inserting an extra TiN layer between two Ti layers) may result in limiting grain formation to smaller sized Ti grains as compared to those formed by deposition of a continuous, thicker layer of Ti. A smoother bottom electrode layer stack with smaller Ti grains in turn results in smoother bottom cavity layer once processing is completed, and can therefore improve device reliability performance.

By way of further illustration, reference may be made generally to FIGS. 4-1 through 4-3, which are a series of cross-sectional views illustrating some processing operations that may be performed in fabricating a micromachined ultrasonic transducer device 400 according to an embodiment. For the sake of illustration and ease of comparison with respect to the earlier described structures, like elements are designated with like reference numbers. As shown in FIG. 4-1, a transducer bottom electrode layer 404 is disposed over the substrate 102. Similar to the transducer bottom electrode layer 104 of FIG. 2-1, the transducer bottom electrode layer 404 includes a first TiN layer 106 (seed layer) and a second layer 110 of TiN (which, again, may serve as a capping layer). However, instead of a single continuous thick layer of Ti disposed between TiN layers 106 and 110, the embodiment of FIG. 4-1 further includes an additional TiN layer 406 formed about midway along the thickness of the combined Ti material, which is now effectively two individual thinner layers, 108-1 and 108-2. It should be appreciated at this point that the individual layer thicknesses depicted in the various figures are not shown to scale and are only for illustrative purposes.

Figure 5:
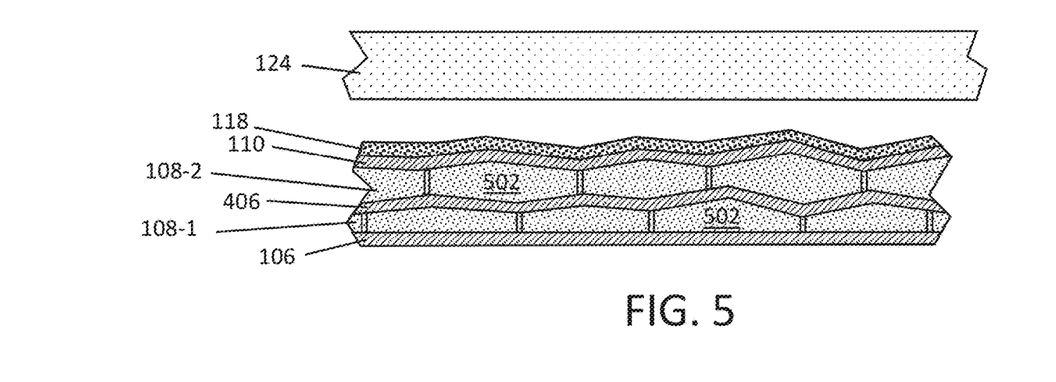
FIG. 5 is an enlarged cross-sectional view of a portion of the micromachined ultrasonic transducer device as shown in FIG. 4-3.

As was the case in FIG. 2-2, patterning and etching of the bottom electrode layer 404 in FIG. 4-2 does not have any appreciable impact on layer integrity. However, following remaining downstream processing operations, the completed transducer device 400 shown in FIG. 4-3 still does not suffer the same adverse surface conditions as those shown in FIGS. 2-3 and 2-3A. A more detailed view of the transducer bottom electrode layer stack is shown in FIG. 5. Here, the individual metal grains 502 formed in Ti layer 108-1 and in Ti layer 108-2 are not only individually smaller as a whole (due the smaller thickness of each Ti layer) with respect to the grains 302 of FIG. 3A, but the grain growth origins are also randomized from the lower Ti layer 108-1 to the upper Ti layer 108-2. Given these effects, the new transducer bottom electrode layer stack may be much smoother and less susceptible to certain deleterious effects such as was described in connection with FIG. 3B.

Figure 6:
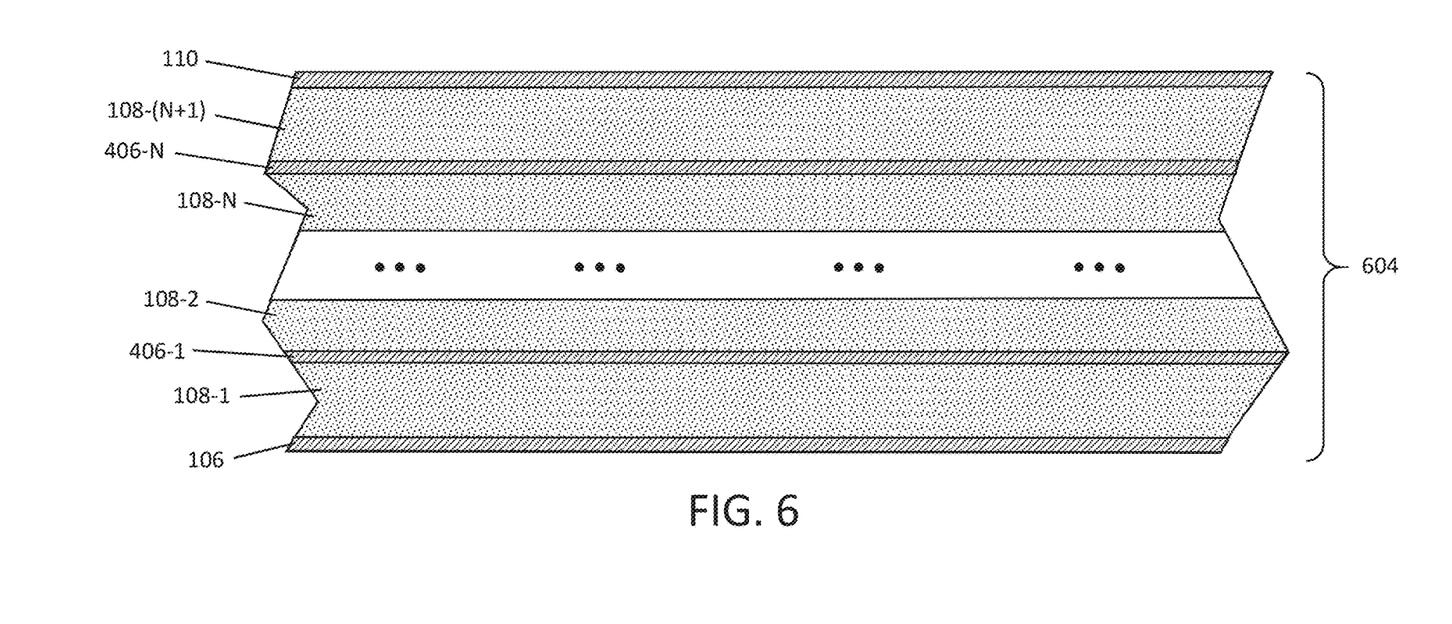
FIG. 6 is a cross-sectional view of a bottom electrode layer having a multiple sandwiched material layer stack, in accordance with an embodiment.

Referring now to FIG. 6, there is shown a cross-sectional view of a bottom electrode layer 604 having a multiple sandwiched material layer stack, in accordance with another embodiment. It will be appreciated that the above described "double sandwiched" structure concept may be further expanded so as to include additional numbers of intermediate TiN layers 406 between the bottom seed TiN layer 106 and the top capping TiN layer 110. Thus, if there are N number of intermediate TiN layers used in the bottom electrode layer 604 (labeled 406-1 . . . 406-N in FIG. 6), the Ti material will be separated into even thinner N+1 discrete layers (labeled 108-1 through 108-(N+1) in FIG. 6). An advantageous number of intermediate TiN layers used in this manner may depend upon a balance between processing steps and/or throughput efficiency with a specific requirement for surface roughness limitations.

Figure 7:
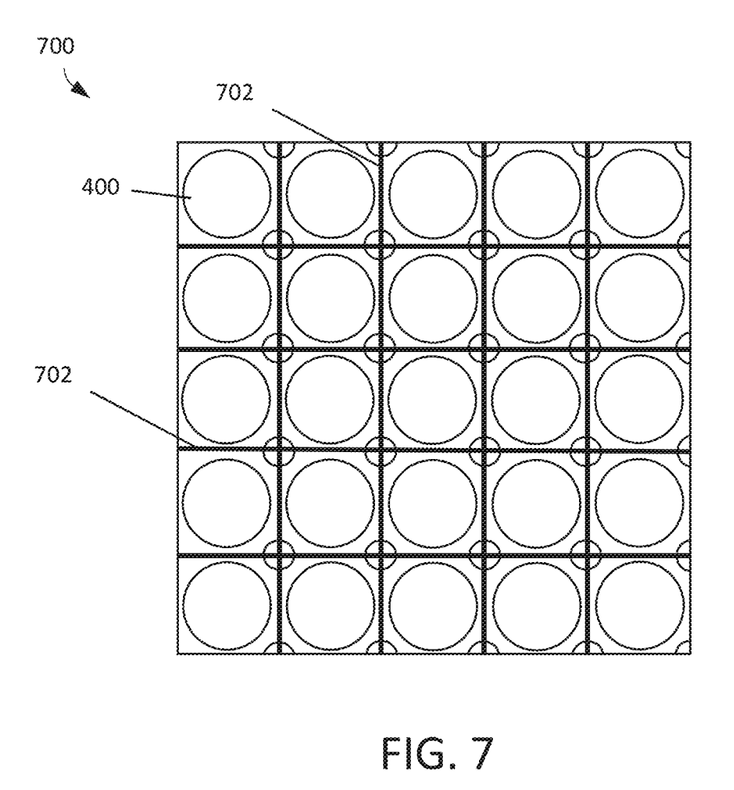
FIG. 7 is a top view of an example ultrasound device formed using any of the micromachined ultrasonic transducer devices described herein.

FIG. 7 illustrates a top view of an example ultrasonic transducer device 700 formed using any of the exemplary transducer structure embodiments described herein. As illustrated, the transducer device includes an array of individual transducers 400, such as those respectively described above in conjunction with FIG. 4. The specific number of transducers 400 shown in FIG. 7 should not be construed in any limiting sense, and may include any number suitable for a desired imaging application, which may be for example on the order of tens, hundreds, thousands, tens of thousands or more. FIG. 7 further illustrates an example location of metal 702 that may distribute an electrical signal to the membranes (upper electrodes) of the transducers 400.

As will thus be appreciated, the above described embodiments, whether implemented alone or in combination with one another, may provide certain benefits such as (for example) improved process margins and wafer bonding yield and device reliability performance. As such, they may be particularly desirable for volume manufacturing of ultrasonic transducer devices and systems incorporating such devices.

Various aspects of the present technology may be used alone, in combination, or in a variety of arrangements not explicit in the embodiments described in the foregoing and therefore are not limited in their application to the details and arrangement of components set forth in the foregoing description or illustrated in the drawings. For example, aspects described in one embodiment may be combined in any manner with aspects described in other embodiments.

Also, some aspects of the technology may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An ultrasonic transducer device, comprising:
   a bottom electrode layer of a transducer cavity disposed over a substrate, the bottom electrode further comprising:
   a bottom layer of a first type metal;
   a top layer of the first type metal;
   a second type metal disposed between the bottom layer and the top layer;
   at least one intermediate layer of the first type metal disposed between the bottom layer and the top layer, the at least one intermediate layer configured so as to separate at least two discrete layers of the second type metal; and
   a bottom cavity layer formed on the bottom electrode layer, the bottom cavity layer including a chemical vapor deposition (CVD) $SiO_2$ layer and an atomic layer deposition (ALD) $Al_2O_3$ layer formed on the $SiO_2$ layer.

2. The ultrasonic transducer device of claim 1, wherein the first type metal comprises titanium nitride (TiN).

3. The ultrasonic transducer device of claim 2, wherein the second type metal comprises titanium.

4. The ultrasonic transducer device of claim 1, wherein the bottom layer, the top layer and the at least one intermediate layer have a thickness of about 10 nanometers (nm) to about 30 nm.

5. The ultrasonic transducer device of claim 1, wherein the at least two discrete layers of the second type metal have a total thickness of about 10 nm to about 300 nm.

6. The ultrasonic transducer device of claim 1, further comprising a membrane support layer formed over the bottom cavity layer, the membrane support layer having the transducer cavity defined therein.

7. The ultrasonic transducer device of claim 6, further comprising a membrane bonded to the membrane support layer to seal the cavity.

8. A method of forming an ultrasonic transducer device, the method comprising:
   forming a bottom layer of a first type metal over a substrate;
   forming a second type metal over the bottom layer;
   forming a top layer of the first type metal over the second type metal;
   forming at least one intermediate layer of the first type metal between the bottom layer and the top layer, the at least one intermediate layer configured so as to separate at least two discrete layers of the second type metal, wherein the bottom layer, the at least one intermediate layer, the at least two discrete layers and the top layer define a bottom electrode layer of a transducer cavity; and
   forming a bottom cavity layer on the bottom electrode layer by forming a chemical vapor deposition (CVD)

SiO$_2$ layer on the bottom electrode layer and an atomic layer deposition (ALD) Al$_2$O$_3$ layer on the SiO$_2$ layer.

9. The method of claim 8, wherein the first type metal comprises titanium nitride (TiN).

10. The method of claim 9, wherein the second type metal comprises titanium.

11. The method of claim 8, wherein the bottom layer, the top layer and the at least one intermediate layer have a thickness of about 10 nanometers (nm) to about 30 nm.

12. The method of claim 8, wherein the at least two discrete layers of the second type metal have a total thickness of about 10 nm to about 300 nm.

13. The method of claim 8, further comprising forming a membrane support layer formed over the bottom cavity layer, and defining the transducer cavity in the membrane support layer.

14. The method of claim 13, further comprising bonding a membrane to the membrane support layer to seal the cavity.

* * * * *